United States Patent [19]

Hübsch et al.

[11] Patent Number: 5,120,782
[45] Date of Patent: Jun. 9, 1992

[54] SUBSTITUTED PYRROLO-PYRIDINES PHARMACEUTICALS

[75] Inventors: Walter Hübsch; Rolf Angerbauer; Peter Fey; Hilmar Bischoff, all of Wuppertal; Joachim Bender, Velbert; Delf Schmidt, Wuppertal, all of Fed. Rep. of Germany

[73] Assignee: Bayer Aktiengesellschaft, Leverkusen, Fed. Rep. of Germany

[21] Appl. No.: 724,414

[22] Filed: Jun. 28, 1991

[30] Foreign Application Priority Data

Jul. 13, 1990 [DE] Fed. Rep. of Germany ...... 4022414

[51] Int. Cl.⁵ .................. A61K 31/435; C07D 471/04
[52] U.S. Cl. ..................................... 514/300; 514/81; 546/23; 546/113
[58] Field of Search ............... 546/23, 113; 514/81, 514/300

[56] References Cited

U.S. PATENT DOCUMENTS

| | | | |
|---|---|---|---|
| 4,939,159 | 7/1990 | Anderson et al. | 546/113 |
| 5,025,000 | 6/1991 | Karanewsky | 546/23 |
| 5,034,399 | 7/1991 | Hubsch et al. | 514/300 |

FOREIGN PATENT DOCUMENTS 1595949 2/1970 Fed. Rep. of Germany.

Primary Examiner—Bernard Dentz
Attorney, Agent, or Firm—Sprung Horn Kramer & Woods

[57] ABSTRACT

Substituted pyrrolo-pyridines can be prepared by reduction of the corresponding ketones. They are useful active compounds for medicaments and can be employed, for example, for the treatment of hyperlipoproteinaemia, lipoproteinaemia and arteriosclerosis.

12 Claims, No Drawings

SUBSTITUTED PYRROLO-PYRIDINES PHARMACEUTICALS

The invention relates to substituted pyrrolo-pyridines, to intermediate compounds for their preparation, and to their preparation and their use in medicaments.

It is known that lactone derivatives isolated from fungal cultures are inhibitors of 3-hydroxy-3-methylglutarylcoenzyme A reductase (HMG-CoA reductase) [mevinolin, EP 22,478; US 4,231,938].

Phosphorus-containing HMG-CoA reductase inhibitors having antihypercholesterolaemic activity are additionally published in DE 3,817,298 A1.

New substituted pyrrolo-pyridines of the general formula (I)

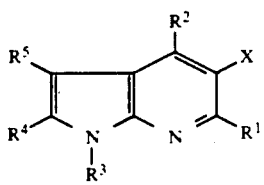

in which
R$^1$ represents straight-chain or branched alkyl having up to 8 carbon atoms, or represents cycloalkyl having 3 to 6 carbon atoms,
R$^2$ represents phenyl which is optionally monosubstituted or disubstituted by identical or different substituents from the series comprising straight-chain or branched alkyl having up to 6 carbon atoms, trifluoromethyl, hydroxymethyl, phenoxy, benzyl, benzyloxy or halogen,
R$^3$ represents hydrogen, represents straight-chain or branched alkyl having up to 10 carbon atoms, which is optionally substituted by cyano, straight-chain or branched alkoxy having up to 6 carbon atoms, halogen, pyridyl, quinolinyl, furyl, thienyl, naphthyl or phenyl, each of which can in turn be substituted by halogen, cyano, nitro, or straight-chain or branched alkyl or alkoxy in each case having up to 6 carbon atoms, represents straight-chain or branched alkenyl or alkynyl in each case having up to 8 carbon atoms, or represents cycloalkyl having 3 to 6 carbon atoms or phenyl,
R$^4$ and R$^5$ are identical or different and represent hydrogen, or represent straight-chain or branched alkyl having up to 6 carbon atoms, which is optionally substituted by hydroxyl, halogen, cyano or alkoxy having up to 4 carbon atoms,
X represents a radical of the formula —A—B,
in which
A denotes a group of the formula —CH$_2$—CH$_2$— or —CH=CH—,
B denotes a group of the formula

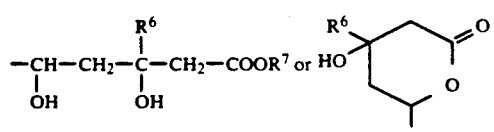

in which
R$^6$ denotes hydrogen or straight-chain or branched alkyl having up to 10 carbon atoms and
R$^7$ denotes hydrogen or straight-chain or branched alkyl having up to 10 carbon atoms, which can be substituted by phenyl, or denotes aryl having 6 to 10 carbon atoms or a cation, or represents a radical of the formula

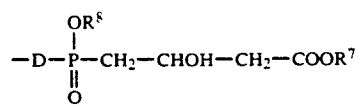

in which
D denotes a radical of the formula —(CH$_2$)$_t$, —CH=CH—, —C≡C— or —CH$_2$—O—, in which the latter is bonded to the phosphorus atom via O,
R$^7$ has the abovementioned meaning of R$^7$,
R$^8$ denotes hydrogen or straight-chain or branched alkyl having up to 4 carbon atoms,
t denotes the number 1 or 2,
and their salts have been found.

If R$^7$ forms an ester radical with the carboxyl group, a physiologically tolerable ester radical is preferably meant by this, which is easily hydrolyzed in vivo to give a free carboxyl group and a corresponding physiologically tolerable alcohol. These include, for example, alkyl esters (C$_1$ to C$_6$) and aralkyl esters (C$_7$ to C$_{10}$), preferably (C$_1$-C$_4$)-alkyl esters and benzyl esters. Moreover, the following ester radicals may be mentioned: methyl esters, ethyl esters, propyl esters and benzyl esters.

If R$^7$ represents a cation, a physiologically tolerable metal cation or ammonium cation is preferably meant. Preferred cations in this connection are alkali metal cations or alkaline earth metal cations such as, for example, sodium, potassium, magnesium or calcium cations, and also aluminum or ammonium cations, as well as nontoxic substituted ammonium cations formed from amines such as (C$_1$-C$_4$)-dialkylamines, (C$_1$-C$_4$)-trialkylamines, procaine, dibenzylamine, N,N'-dibenzylethylenediamine, N-benzyl-β-phenylethylamine, N-methylmorpholine or N-ethylmorpholine, 1-ephenamine, dihydroabietylamine, N,N'-bis-dihydroabietylethylenediamine, N-lower alkylpiperidine and other amines which can be used for the formation of salts.

R$^8$ can likewise represent one of the abovementioned physiologically tolerable metal cations or ammonium cations.

Surprisingly, the substituted pyrrolo-pyridines according to the invention show a superior inhibitory action on HMG-CoA reductase (3-hydroxy-3-methylglutaryl-coenzyme A reductase).

Preferred compounds of the general formula (I) are those
in which
R$^1$ represents straight-chain or branched alkyl having up to 6 carbon atoms, or represents cyclopropyl, cyclopentyl or cyclohexyl,
R$^2$ represents phenyl which is optionally substituted by straight-chain or branched alkyl having up to 4 carbon atoms, trifluoromethyl, fluorine, chlorine or bromine,
R$^3$ represents hydrogen, represents straight-chain or branched alkyl having up to 8 carbon atoms, which is optionally substituted by cyano, straight-chain or branched alkoxy having up to 4 carbon atoms, fluorine, chlorine, bromine, pyridyl or phenyl, each of which can in turn be substituted by fluorine, chlorine, bromine cyano, nitro, straight-chain or branched alkyl or alkoxy in each case having up to 4 carbon atoms, represents straight-chain or branched alkenyl or alkynyl in each case having up to 6 carbon atoms, or represents cyclopropyl, cyclopentyl, cyclohexyl or phenyl, $R^4$ and $R^5$ represent hydrogen, X represents a radical of the formula —A—B, in which A denotes a group of the formula —$CH_2$—$CH_2$— or —CH=CH—, B denotes a group of the formula

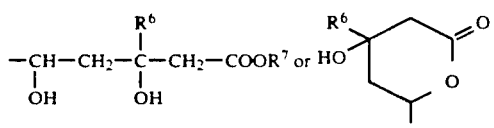

in which $R^5$ denotes hydrogen and $R^7$ denotes hydrogen or straight-chain or branched alkyl having up to 8 carbon atoms or benzyl, or denotes phenyl or a cation, and their salts.

Particularly preferred compounds of the general formula (I) are those in which $R^1$ represents straight-chain or branched alkyl having up to 4 carbon atoms or cyclopropyl, $R^2$ represents phenyl which is optionally substituted by methyl, trifluoromethyl, fluorine or chlorine, $R^3$ represents hydrogen, represents straight-chain or branched alkyl having up to 6 carbon atoms, which is optionally substituted by cyano, methoxy, fluorine, pyridyl or phenyl, represents straight-chain or branched alkenyl or alkynyl in each case having up to 4 carbon atoms, or represents cyclopentyl or cyclohexyl, $R^4$ and $R^5$ represent hydrogen, X represents a radical of the formula —A—B, in which A denotes a group of the formula —$CH_2$—$CH_2$— or —CH=CH—, B denotes a group of the formula

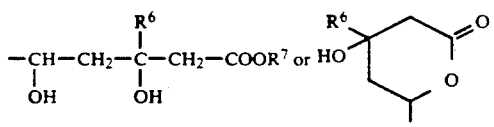

in which $R^5$ denotes hydrogen and $R^7$ denotes hydrogen, methyl, ethyl, propyl, isopropyl, butyl, isobutyl, tert-butyl or benzyl, or denotes a sodium, potassium, calcium, magnesium or ammonium ion, and their salts.

The substituted pyrrolo-pyridines of the general formula (I) according to the invention have several asymmetric carbon atoms and can therefore exist in various stereochemical forms. The invention relates both to the individual isomers and to their mixtures.

Depending on the meaning of the radicals given under the substituent X, different stereoisomers result, which is explained in more detail as exemplified by the radical —A—B as follows:

a) If the group —A— represents a group of the formula —CH=CH—, the compounds according to the invention can exist in two stereoisomeric forms which can have the E-configuration (II) or Z-configuration (III) of the double bond:

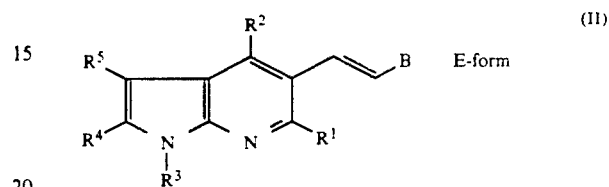

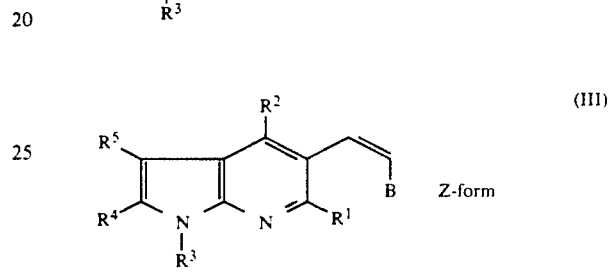

in which $R^1$, $R^2$, $R^3$, $R^4$, $R^5$ and B have the abovementioned meanings.

Preferred compounds of the general formula (I) are those which have the E-configuration (II).

b) If the radical —B represents a group of the formula

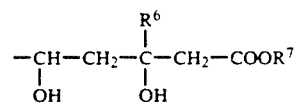

the compounds of the general formula (I) have at least two asymmetric carbon atoms, namely the two carbon atoms to which the hydroxyl groups are bonded. Depending on the relative position of these hydroxyl groups to one another, the compounds according to the invention can be present in the erythro-configuration (IV) or in the threo-configuration (V).

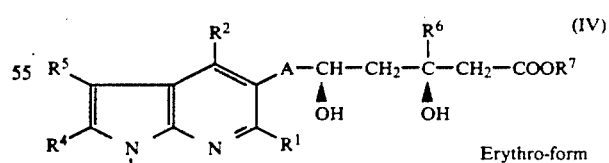

Erythro-form

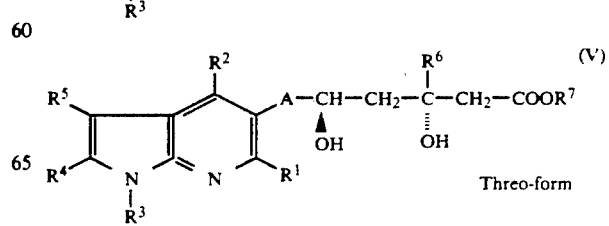

Threo-form

In each case, two enantiomers, namely the 3R,5S-isomer or the 3S,5R-isomer (erythro-form) and the 3R,5R-isomer and the 3S,5S-isomer (threo-form) in turn exist both of the compounds in the erythro- and in the threo-configuration.

The isomers in the erythro-configuration are preferred in this case, particularly preferably the 3R,5S-isomer and the 3R,5S-3S,5R-racemate.

c) If the radical —B— represents a group of the formula

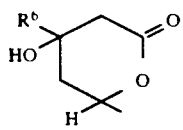

the substituted pyrrolo-pyridines have at least two asymmetric carbon atoms, namely the carbon atom to which the hydroxyl group is bonded, and the carbon atom to which the radical of the formula

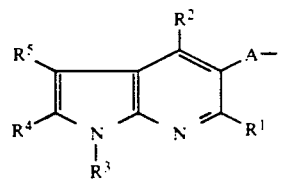

is bonded. Depending on the position of the hydroxyl group to the free valency on the lactone ring, the substituted pyrrolo-pyridines can be present as cis-lactones (VI) or as trans-lactones (VII).

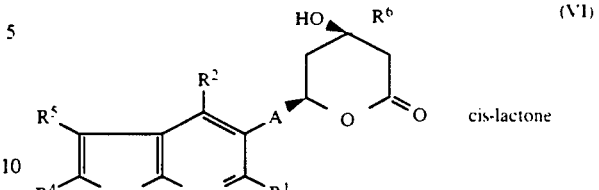

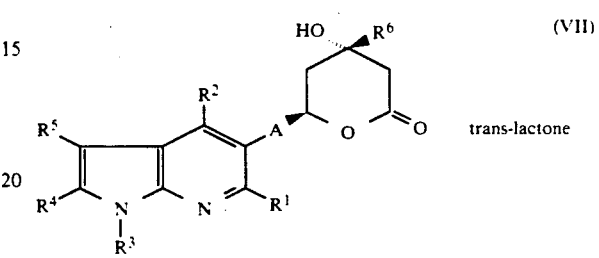

In each case, two isomers, namely the 4R,6R-isomer or the 4S,6S-isomer (cis-lactone), and the 4R,6S-isomer or 4S,6R-isomer (trans-lactone) in turn exist both of the cis-lactone and the trans-lactone. Preferred isomers are the trans-lactones. The 4R,6S-isomer (trans) and the 4R,6S-4S,6R-racemate are particularly preferred in this case.

The following isomeric forms of the substituted pyrrolopyridines may be mentioned as examples:

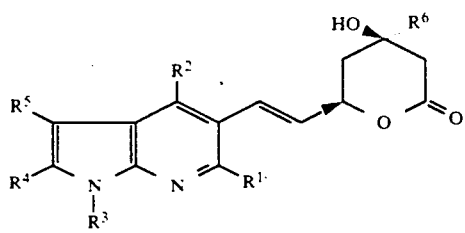

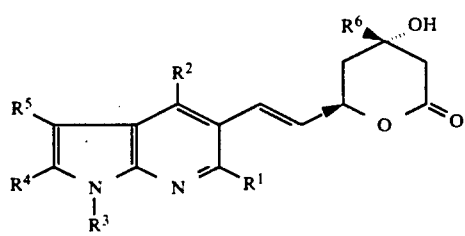

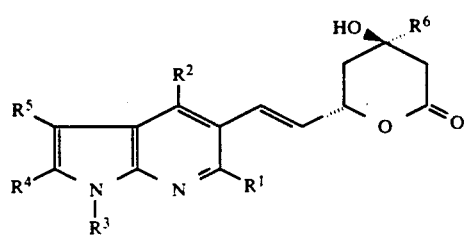

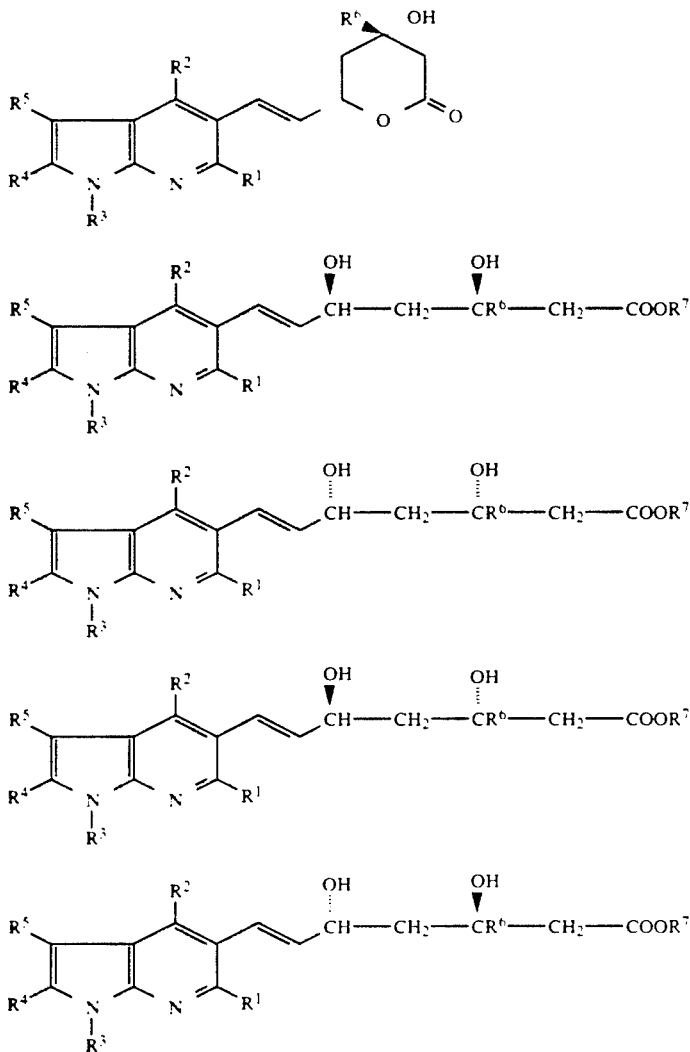

The substituted pyrrolo-pyridines of the general formula (I) are prepared by a process in which ketones of the general formula (VIII)

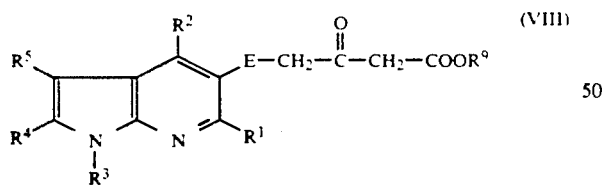

in which
R¹, R², R³, R⁴ and R⁵ have the abovementioned meanings,
R⁹ represents alkyl,
and
E represents a group $$-D-\overset{\overset{OR^8}{|}}{\underset{\underset{O}{\|}}{P}}- \quad (VIIIa)$$

or

are reduced, and
in the case of the preparation of the acids, the esters are hydrolyzed,
in the case of the preparation of the lactones, the carboxylic acids are cyclized,
in the case of the preparation of the ethylene compounds (A=—CH₂—CH₂—), the ethenyl compounds (A=—CH=CH—) are hydrogenated by customary methods,
and, if appropriate, isomers are separated.

The process according to the invention can be illustrated by the following equation:

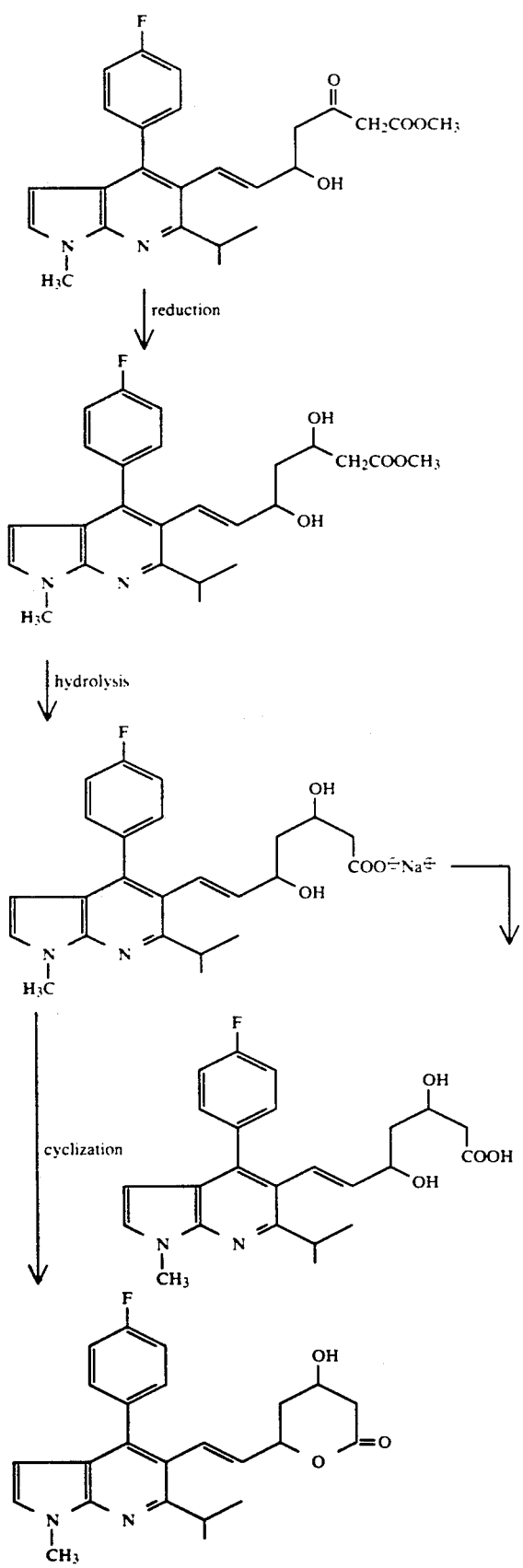

The reduction can be carried out with the customary reducing agents, preferably with those which are suitable for the reduction of ketones to hydroxyl compounds. In this case, reduction with metal hydrides or complex metal hydrides in inert solvents, if appropriate in the presence of a trialkylborane, is particularly suitable. The reduction is preferably carried out with complex metal hydrides such as, for example, lithium borohydride, sodium borohydride, potassium borohydride, zinc borohydride, lithium trialkylborohydrides, sodium trialkylborohydrides, sodium cyanoborohydride or lithium aluminum hydride The reduction is very particularly preferably carried out with sodium borohydride in the presence of triethylborane.

Suitable solvents in this connection are the customary organic solvents which do not change under the reaction conditions. These preferably include ethers such as, for example, diethyl ether, dioxane, tetrahydrofuran or dimethoxyethane, or halogenated hydrocarbons such as, for example, dichloromethane, trichloromethane, tetrachloromethane, 1,2-dichloroethane, or hydrocarbons such as, for example, benzene, toluene or xylene. It is also possible to employ mixtures of the solvents mentioned.

If E represents the radical of the formula (VIIIa), alcohols such as methanol, ethanol or propanol, preferably ethanol, are employed.

The reduction of the ketone group to the hydroxyl group is particularly preferably carried out under conditions in which the other functional groups such as, for example, the alkoxycarbonyl group, are not changed.

The use of sodium borohydride as the reducing agent is particularly suitable for this purpose, in the presence of triethylborane in inert solvents such as, preferably, ethers.

The reduction is in general carried out in a temperature range from $-80°$ C. to $+30°$ C., preferably from $-78°$ C. to $0°$ C.

The process according to the invention is in general carried out at normal pressure. However, it is also possible to carry out the process at reduced pressure or at elevated pressure (for example in a range from 0.5 to 5 bar).

In general, the reducing agent is employed in an amount from 1 to 2 mols preferably from 1 to 1.5 mols relative to 1 mol of the keto compound.

Under the abovementioned reaction conditions, the carbonyl group is in general reduced to the hydroxyl group without reduction of the double bond to a single bond taking place.

In order to prepare compounds of the general formula (I) in which A represents an ethylene grouping, the reduction of the ketones (VIII) can be carried out under those conditions under which both the carbonyl group and the double bond are reduced.

Moreover, it is also possible to carry out the reduction of the carbonyl group and the reduction of the double bond in two separate steps.

The carboxylic acids in the context of the general formula (I) correspond to the formula (Ia)

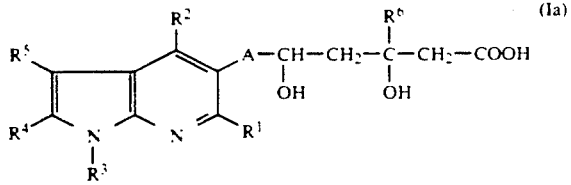

in which
R$^1$, R$^2$, R$^3$, R$^4$, R$^5$, R$^6$ and A have the abovementioned meanings.

The carboxylic acid esters in the context of the general formula (I) correspond to the formula (Ib)

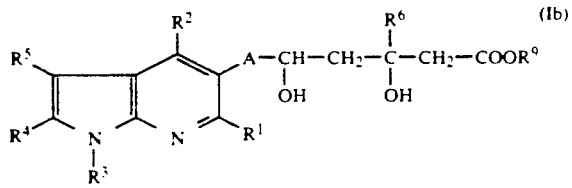

in which
R$^1$, R$^2$, R$^3$, R$^4$, R$^5$, R$^6$ and A have the abovementioned meanings,
and
R$^9$ represents alkyl.

The salts of the compounds according to the invention in the context of the general formula (I) correspond to the formula (Ic)

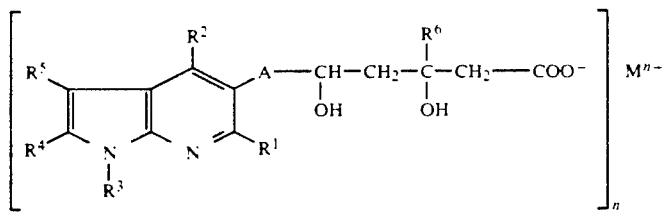

in which
R$^1$, R$^2$, R$^3$, R$^4$, R$^5$, R$^6$ and A have the abovementioned meanings,
and
M$^{n+}$ represents a cation.

The lactones in the context of the general formula (I) correspond to the formula (Id)

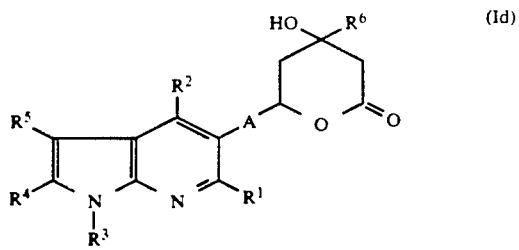

in which
R$^1$, R$^2$, R$^3$, R$^4$, R$^5$, R$^6$ and A have the abovementioned meanings.

In order to prepare the carboxylic acids of the general formula (Ia) according to the invention, the carboxylic acid esters of the general formula (Ib) or the lactones of the general formula (Id) are in general hydrolyzed by customary methods. The hydrolysis is in general carried out by treating the esters or the lactones with customary bases in inert solvents, the salts of the general formula (Ic) in general being formed first, which can then be converted into the free acids of the general formula (Ia) in a second step by treatment with acid.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium ethoxide, sodium methoxide, potassium methoxide, potassium ethoxide or potassium tert-butoxide. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is in general carried out in a temperature range of 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mols preferably from 1 to 1.5 mols relative to 1 mol of the ester or the lactone. Molar amounts of the reactants are particularly preferably used.

When carrying out the reaction, the salts (Ic) of the compounds according to the invention are formed in the first step as intermediates which can be isolated. The acids (Ia) according to the invention are obtained by treating the salts (Ic) with customary inorganic acids. These preferably include mineral acids such as, for example, hydrochloric acid, hydrobromic acid, sulphuric acid or phosphoric acid. In this connection, it has proved advantageous in the preparation of the carboxylic acids (Ia) to acidify the basic reaction mixture from the hydrolysis in a second step without isolating the salts. The acids can then be isolated in a customary manner.

In order to prepare the lactones of the formula (Id) according to the invention, the carboxylic acids (Ib) according to the invention are in general cyclized by customary methods, for example by heating the corresponding acid in inert organic solvents, if appropriate in the presence of molecular sieve.

Suitable solvents in this connection are hydrocarbons such as benzene, toluene, xylene, mineral oil fractions, or tetralin or diglyme or triglyme. Benzene, toluene or xylene are preferably employed. It is also possible to employ mixtures of the solvents mentioned. Hydrocarbons are particularly preferably used, in particular toluene, in the presence of molecular sieve.

The cyclization is in general carried out in a temperature range of $-40°$ C. to $+200°$ C., preferably from $-25°$ C. to $+50°$ C.

The cyclization is in general carried out at normal pressure, but it is also possible to carry out the process at reduced pressure or at elevated pressure (for example in a range from 0.5 to 5 bar).

Moreover, the cyclization is also carried out in inert organic solvents, with the aid of cyclizing or dehydrating agents. Carbodiimides are preferably used in this case as dehydrating agents. The preferred carbodiimides employed are N,'-dicyclohexylcarbodiimide, N-cyclohexyl-N'-[2-(N''-methylmorpholinium)ethyl]-carbodiimide paratoluenesulphonate or N-(3-dimethylaminopropyl)-N'-ethylcarbodiimide hydrochloride.

Suitable solvents in this connection are the customary organic solvents. These preferably include ethers such as diethyl ether, tetrahydrofuran or dioxane, or chlorohydrocarbons such as methylene chloride, chloroform or carbon tetrachloride, or hydrocarbons such as benzene, toluene, xylene or mineral oil fractions. Chlorohydrocarbons such as, for example, methylene chloride, chloroform or carbon tetrachloride, or hydrocarbons such as benzene, toluene, xylene, or mineral oil fractions are particularly preferred. Chlorohydrocarbons such as, for example, methylene chloride, chloroform or carbon tetrachloride are particularly preferably employed.

The reaction is in general carried out in a temperature range of from $0°$ C. to $+80°$ C., preferably from $+10°$ C. to $+50°$ C.

When carrying out the cyclization, it has proved advantageous to employ the cyclization method using carbodiimides as dehydrating agents.

The separation of the isomers into the stereoisomerically homogeneous constituents is in general carried out by customary methods such as are described, for example, by E. L. Eliel, Stereochemistry of Carbon Compounds, McGraw Hill, 1962. In this connection, the separation of the isomers from the racemic lactone stage is preferred. The racemic mixture of the trans-lactones (VII) is particularly preferably converted in this case by treating either with $D-(+)-$ or $L-(-)-\alpha-$methylbenzylamine by customary methods into the diastereomeric dihydroxyamides (Ie)

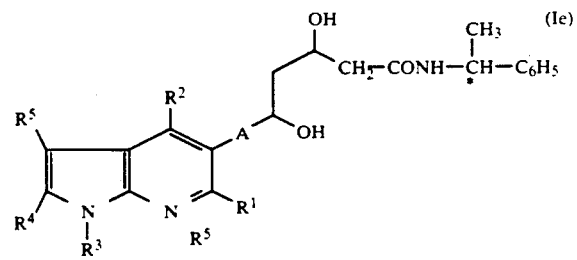

which can then be separated into the individual diastereomers by chromatography or crystallization, as is customary. Subsequent hydrolysis of the pure diastereomeric amides by customary methods, for example by treating the diastereomeric amides with inorganic bases such as sodium hydroxide or potassium hydroxide in water and/or organic solvents such as alcohols, for example methanol, ethanol, propanol or isopropanol, gives the corresponding enantiomerically pure dihydroxy acids (Ia), which can be converted into the enantiomerically pure lactones by cyclization as described above. In general, it is true of the preparation of the compounds of the general formula (I) according to the invention in enantiomerically pure form that the configuration of the final products according to the method described above is dependent on the configuration of the starting materials.

The isomer separation is illustrated by way of example in the following scheme:

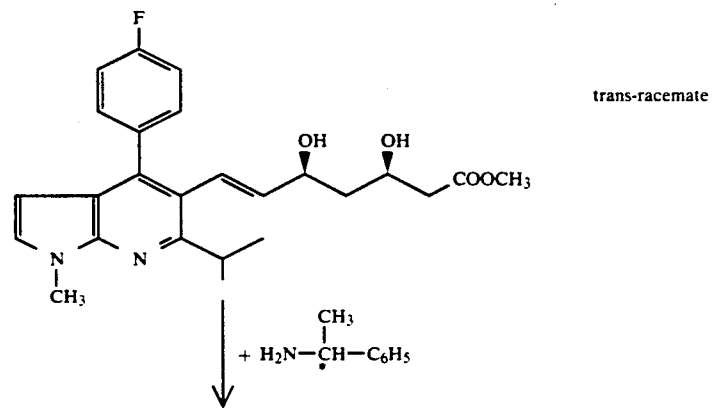

trans-racemate

-continued

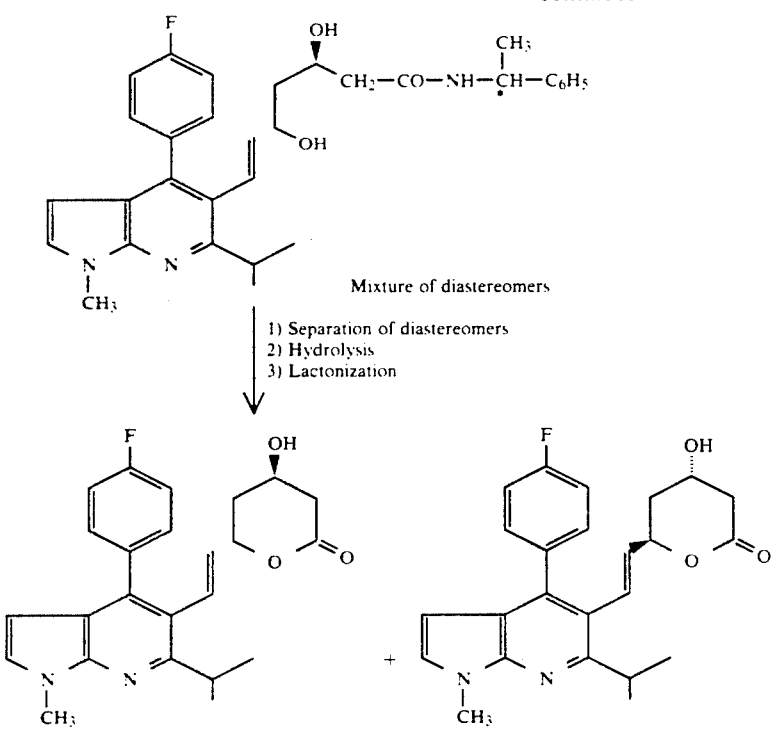

Mixture of diastereomers

1) Separation of diastereomers
2) Hydrolysis
3) Lactonization

The ketones of the formula (VIIIa) employed as starting materials are new and can be prepared in analogy to the process described in DE 3,817,298 A1.

The ketones (VIIIb) employed as starting materials are new.

A process for the preparation of the ketones of the general formula (VIIIb) according to the invention

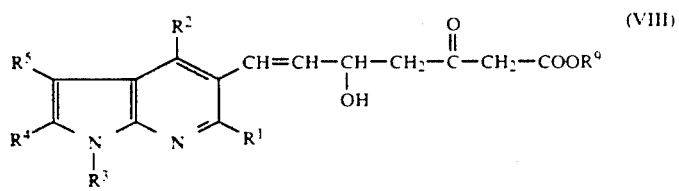 (VIII)

in which
$R^1$, $R^2$, $R^3$, $R^4$, $R^5$ and $R^6$ have the abovementioned meanings, has been found, which is characterized in that aldehydes of the general formula (IX)

(IX)

in which
$R^1$, $R^2$, $R^3$, $R^4$ and $R^5$ have the abovementioned meanings, are reacted in inert solvents with acetonacetic acid esters of the general formula (X)

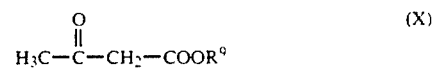 (X)

in which
$R^9$ has the abovementioned meaning, in the presence of bases.

The process according to the invention can be illustrated, for example, by the following equation:

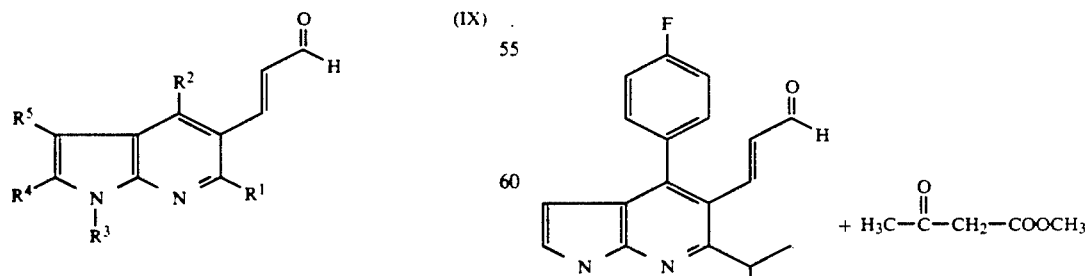

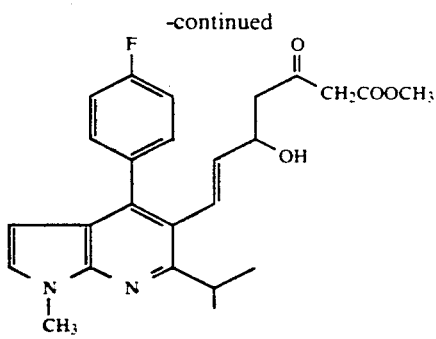

Suitable bases in this connection are the customary strongly basic compounds. These preferably include organolithium compounds such as, for example, n-butyllithium, sec-butyllithium, tert-butyllithium or phenyllithium, or amides, such as, for example, lithium diisopropylamide, sodium amide or potassium amide, or lithium hexamethyldisilylamide, or alkali metal hydrides such as sodium hydride or potassium hydride. It is also possible to employ mixtures of the bases mentioned. N-Butyllithium or sodium hydride or a mixture thereof is particularly preferably employed.

Suitable solvents in this connection are the customary organic solvents which do not change under the reaction conditions. These preferably include ethers such as diethyl ether, tetrahydrofuran, dioxane or dimethoxyethane, or hydrocarbons such as benzene, toluene, xylene, cyclohexane, hexane or mineral oil fractions. It is also possible to employ mixtures of the solvents mentioned. Ethers such as diethyl ether or tetrahydrofuran are particularly preferably used.

The reaction is in general carried out in a temperature range from −80° C. to +50° C., preferably from −20° C. to room temperature.

The process is in general carried out at normal pressure, but it is also possible to carry out the process at reduced pressure or at elevated pressure, for example in a range from 0.5 to 5 bar.

When carrying out the process, the acetoacetic acid ester is in general employed in an amount from 1 to 2, preferably from 1 to 1.5 mols relative to 1 mol of the aldehyde.

The acetoacetic acid esters of the formula (X) employed as starting materials are known or can be prepared by known methods [Beilstein's Handbuch der organischen Chemie (Beilstein's Handbook of Organic Chemistry) III, 632; 438].

Examples of acetoacetic acid esters which may be mentioned for the process according to the invention are: methyl acetoacetate, ethyl acetoacetate, propyl acetoacetate or isopropyl acetoacetate.

The preparation of the aldehydes of the general formula (IX) employed as starting materials is illustrated by way of example as follows for the case in which X represents the group —A—B:

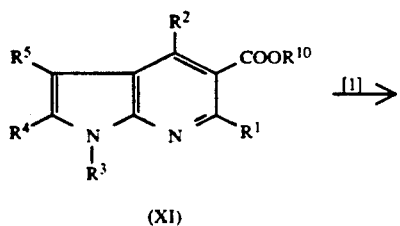

[A]

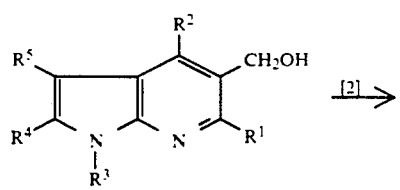

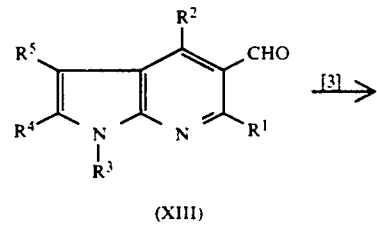

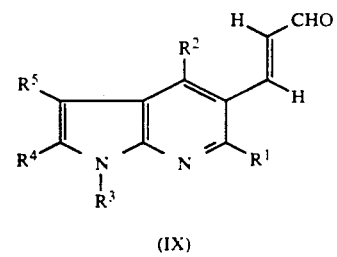

In this connection, according to scheme A, pyrrolopyridines of the formula (XI), in which $R^{10}$ represents alkyl having up to 4 carbon atoms, are reduced to the hydroxymethyl compounds (XII) in a first step [1] in inert solvents such as ethers, for example diethyl ether, tetrahydrofuran or dioxane, preferably tetrahydrofuran, using metal hydrides as reducing agents, for example lithium aluminum hydride, sodium cyanoborohydride, sodium aluminum hydride, diisobutylaluminum hydride or sodium bis-(2-methoxyethoxy)-dihydroaluminate, in temperature ranges from −70° C. to +100° C., preferably from −70° C. to room temperature, or from room temperature to 70° C., depending on the reducing agent used. Reduction is preferably carried out with diisobutylaluminum hydride or with lithium aluminum hydride in tetrahydrofuran in a temperature range from room temperature to 80° C. The hydroxymethyl compounds (XII) are oxidized to the aldehydes (XIII) by customary methods in a second step [2]. The oxidation can be carried out, for example, with pyridinium chlorochromate, optionally in the presence of alumina, in inert solvents such as chlorohydrocarbons, preferably methylene chloride, in a temperature range from 0° C to 60° C, preferably at room temperature, or else with trifluoroacetic anhydride/dimethyl sulphoxide by the customary methods of Swern oxidation. The aldehydes (XIII) are reacted to give the aldehydes (IX) in a third step [3]with diethyl 2-(cyclohexylamino)-vinylphosphonate in the presence of sodium hydride in inert solvents such as ethers, for example diethyl ether, tetrahydrofuran or dioxane, preferably in tetrahydrofuran, in a temperature range from −20° C. to +40° C., preferably from −5° C. to room temperature.

The 2H-pyrrolo-pyridines (XI) employed as starting materials in this connection are in general obtained according to scheme [B]by first oxidizing the dihydropyridines of the formula XIV, in which $R^{10}$ and $R^{10'}$ are identical or different and have the abovementioned meaning, to the corresponding pyridines of the formula (XV), then first converting the ester function (COOR¹⁰′) into the corresponding hydroxymethyl compounds (XVI) by reduction and then oxidizing to the corresponding aldehydes (XVII) and in a last step cyclizing by conventional methods.

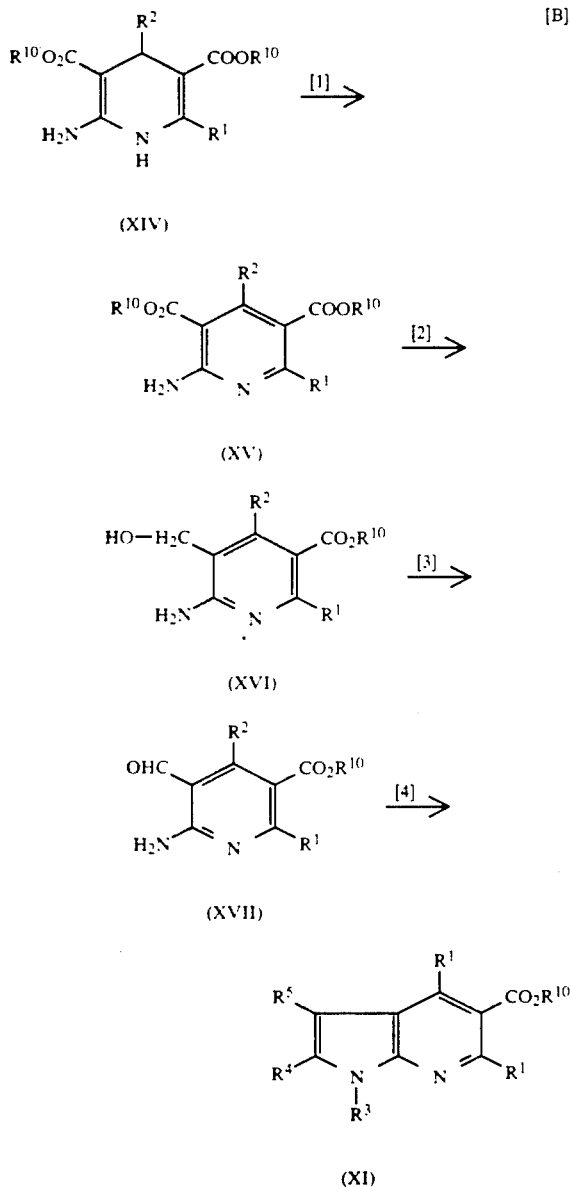

The dihydropyridines employed as starting materials in this connection are new in some cases or known and can be prepared by known methods, for example by condensation of ethoxycarbonyl-acetamidine hydrochloride with (4-fluorophenyl)-2-methoxycarbonyl-4-methyl-pent-1-en-3-one [compare additionally EP-A 88,276, DE-A 2,847,236]. The oxidation of the dihydropyridines (XIV) to give the pyrrolo-pyridines (XI) can be carried out, for example, with chromic oxide in glacial acetic acid in a temperature range from −20° C. to +150° C., preferably at reflux temperature, or with 2,3-dichloro-5,6-dicyano-p-benzoquinone as the oxidizing agent in inert solvents such as chlorohydrocarbons, preferably methylene chloride in a temperature range from 0° C. to +100° C., preferably at room temperature.

The reduction to give the hydroxymethyl compounds of the formula (XVI) [step 2] is carried out using suitable reducing agents, such as, for example, lithium aluminum hydride, diisobutylaluminum hydride or sodium bis(2-methoxyethoxy)-dihydroaluminate in inert solvents, such as, for example, tetrahydrofuran.

The oxidation [step 3] to give the corresponding aldehydes (XVII) is carried out by the abovementioned method.

The cyclization [step 4] is carried out by a Wittig reaction, if appropriate with substituted ($R^4/R^5 \neq H$) phosphonium or phosphorylidene, for example with methoxymethyltriphenylphosphonium bromide, in the presence of a base in aprotic solvents, followed by hydrolysis in aqueous acid.

Suitable bases are alkali metal hydrides and amides, such as, for example, sodium amide or sodium hydride, or organic lithium compounds such as, for example, butyllithium or alkoxides such as potassium tert-butoxide. Sodium amide is preferred.

Suitable solvents are the customary aprotic organic solvents such as, for example, tetrahydrofuran, dimethylformamide or dimethyl sulphoxide. Tetrahydrofuran is preferred.

The base is employed in an amount of 1 to 4, preferably of 1 to 2 mol equivalents.

Acids employed in the hydrolysis are aqueous mineral acids, preferably half-concentrated hydrochloric acid. The hydrolysis is carried out in a temperature range from 0° to 100° C., preferably at 60° to 100° C.

The compounds of the general formula (I) according to the invention have useful pharmacological properties and can be employed in medicaments. In particular, they are inhibitors of 3-hydroxy-3-methyl-glutaryl-coenzyme A (HMG-CoA) reductase and, as a result of this, inhibitors of cholesterol biosynthesis. They can therefore be employed for the treatment of hyperlipoproteinaemia, lipoproteinaemia or arteriosclerosis. The active compounds according to the invention additionally cause a lowering of the cholesterol content in the blood.

The enzyme activity determination was carried out as modified by G. C. Ness et al., Archives of Biochemistry and Biophysics 197, 493–499 (1979). Male Rico rats (body weight 300–400 g) were treated with altromin powdered feed, to which 40 g of colestyramine/kg of feed had been added, for 11 days. After decapitation, the livers were removed from the animals and placed on ice. The livers were comminuted and homogenized 3 times in a Potter-Elvejem homogenizsr in 3 volumes of 0.1 M sucrose, 0.05 M KCl, 0.04 M $K_xH_y$ phosphate, 0.03 M ethylene-diaminetetraacetic acid, 0.002 M dithiothreitol (SPE) buffer pH 7.2. The mixture was then centrifuged at 15,000 g for 15 minutes and the sediment was discarded. The supernatant was sedimented at 100,000 g for 75 minutes. The pellet was taken up in 1/4 volumes of SPE buffer, homogenized again and then centrifuged again at 100,000 g for 60 minutes. The pellet was taken up using a 5-fold amount of its volume of SPE buffer, homogenized and frozen and stored at −78° C. (=enzyme solution).

For testing, the test compounds (or mevinolin as a reference substance) were dissolved in dimethylformamide with the addition of 5 vol. % of 1 N NaOH and employed in the enzyme test using 10 μl in various concentrations. The test was begun after 20 minutes pre-incubation of the compounds with the enzyme at 37° C. The test mixture amounted to 0.380 ml and contained 4 μmol of glucose 6-phosphate, 1.1 mg of bovine serum albumin, 2.1 μmol of dithiothreitol, 0.35 μmol of NADP, 1 unit of glucose 6-phosphate dehydrogenase, 35 μmol of $K_xH_y$ phosphate pH 7.2, 20 μl of enzyme preparation and 56 nmol of 3-hydroxy-3-methyl--glutaryl coenzyme A (glutaryl-3-$^{14}$C) of 100,000 dpm.

After an incubation of 60 minutes at 37° C., the mixture was centrifuged and 600 μl of the supernatant was applied to a 0.7×4 cm column packed with a 5-chloride 100-200 mesh (anion exchanger). The column was washed with 2 ml of distilled water and 3 ml of Aquasol was added to the runnings plus washing water and counted in an LKB scintillation counter. $IC_{50}$ values were determined by intrapolation by plotting the percentage inhibition against the concentration of the compound in the test. In order to determine the relative inhibitory potency, the $IC_{50}$ value of the reference substance mevinolin was set at 1 and compared with the simultaneously determined $IC_{50}$ value of the test compound.

| Example No. | in vitro relative activity Mevinolin = 1 |
| --- | --- |
| 1a | 3 |
| 2a | 3 |
| 1b | 3 |
| 2b | 3 |
| 1c | 13 |
| 2c | 3 |
| 1g | 4 |
| 2g | 2 |
| 1f | 17 |
| 2f | 10 |
| 1i | 9 |
| 1h | 33 |
| 2h | 10 |
| 1e | 17 |
| 1d | 27 |
| 1j | 24 |

The present invention also includes pharmaceutical preparations which, in addition to inert, non-toxic, pharmaceutical auxiliaries and excipients, contain one or more compounds of the general formula (I), or which consist of one or more active compounds of the formula (I), and processes for the production of these preparations.

The active compounds of the formula (I) should be present in these preparations in a concentration of 0.1 to 99.5% by weight, preferably of 0.5 to 95% by weight of the total mixture.

In addition to the active compounds of the formula (I), the pharmaceutical preparations can also contain other pharmaceutically active compounds.

The abovementioned pharmaceutical preparations can be prepared by known methods in a customary manner, for example using the auxiliary or auxiliaries or excipient(s).

In general, it has proved advantageous to administer the active compound(s) of the formula (I) in total amounts of about 0.0005 to about 20 mg/kg, preferably in total amounts of about 0.001 mg/kg to 5 mg/kg of body weight every 24 hours, if desired in the form of several individual doses, to achieve the desired results.

However, it may be advantageous to deviate from the amounts mentioned, in particular depending on the species and body weight of the subject to be treated, on individual behavior towards the medicament, the nature and severity of the disease, the type of preparation and administration, and the time or interval at which administration takes place.

STARTING COMPOUNDS

Example I (E)-Z-1-(4-Fluorophenyl)-2-methoxycarbonyl-4-methyl-pent-1-en-3-one

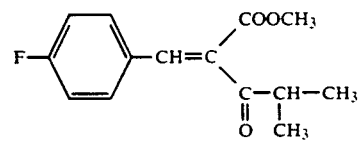

A solution of 22.5 ml (0.223 mol) of piperidine and 13.5 ml (0.23 mol) of acetic acid in 100 ml of isopropanol is added to 576.7 g (4 mol) of methyl isobutyryl-acetate and 496.5 g (4 mol) of 4-fluorobenzaldehyde in 1 l of isopropanol. The mixture is stirred at room temperature for 1 day and concentrated in vacuo, and the residue is distilled in a high vacuum.

Yield: 840.7 g (84% of theory) of yellowish oil,

B.p. 150°-152° C. (4 mbar).

Example II

2-Amino-3-ethoxycarbonyl-4-(4-fluorophenyl)-6-isopropyl-5-methoxycarbonyl-1,4-dihydropyridine

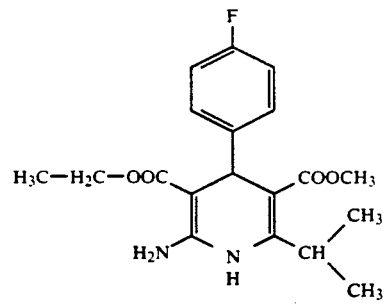

66.6 g (0.4 mol) of ethyl 3,3-diaminoacrylate hydrochloride and 100 g (0.4 mol) of the compound from Example 1 are heated to reflux overnight with 44 ml (0.4 mol) of N-methylmorpholine in 800 ml of isopropanol. The mixture is concentrated in vacuo and the residue is chromatographed in a column (φ20 cm) on 2 kg of silica gel 230-400 mesh using petroleum ether/ethyl acetate (2:1).

Yield 109.7 g (75.7% of theory) of colorless crystals

M.p.: 161° C. (from ether/petroleum ether),

Example III

2-Amino-3-ethoxycarbonyl-4-(4-fluorophenyl)-6-isopropyl-5-methoxycarbonyl-pyridine

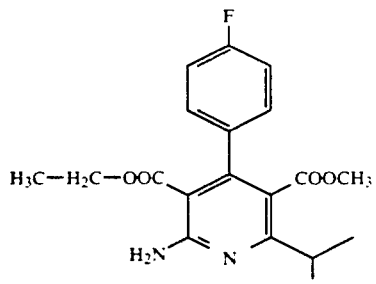

22.7 g (0.1 mol) of 2,3-dichloro-4,5-dicyano-benzoquinone are added to a solution of 36.2 g (0.1 mol) of the compound from Example II in 2 l of dichloromethane and the mixture is stirred at room temperature for 40 min. The suspension is filtered through 1.5 kg of silica gel 230-400 mesh in a glass suction filter and eluted using a mixture of petroleum ether/ethyl acetate 2:1. The eluate is concentrated in vacuo and the residue which remains is thoroughly stirred in ether/petroleum ether and filtered off with suction.

Yield: 31.6 g (88% of theory).
M.p.: 141° C.

Example IV

2-Amino-4-(4-fluorophenyl)-3-hydroxymethyl-6-isopropyl5-methoxycarbonyl-pyridine

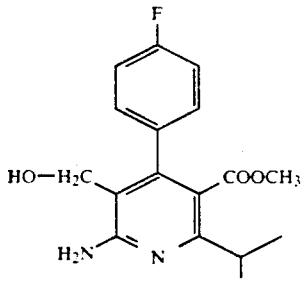

100 ml (0.35 mol) of a 3.5 M solution of sodium bis-(2-methoxy-ethoxy)-dihydroaluminate in toluene are initially introduced under argon into 100 ml of tetrahydrofuran p.a. 63 g (175 mmol) of the compound from Example III dissolved in 700 ml of tetrahydrofuran are added dropwise and the mixture is subsequently stirred at 30° C. for 1 h. 2 l of water are cautiously added dropwise. The phases are separated and the aqueous phase is washed twice with 700 ml of ethyl acetate. The combined organic phases are washed with 500 ml of saturated sodium chloride solution and dried using sodium sulphate. The solution is filtered and concentrated in vacuo. The residue is chromatographed in a column (φ6 cm) on 400 g of silica gel 230–400 mesh using petroleum ether/ethyl acetate (1:1). The eluate is concentrated in vacuo and the residue is thoroughly stirred in ether/petroleum ether.

Yield: 45.2 g (81.2% of theory) of colorless crystals.
M.p.: 137° C.

Example V

2-Amino-4-(4-fluorophenyl)-3-formyl-5-methoxycarbonyl-6-isopropyl-pyridine

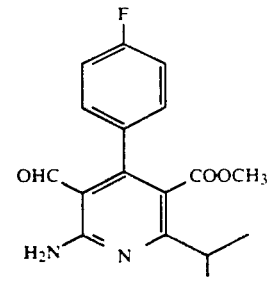

20.7 g (65 mmol) of the compound from Example IV are dissolved in 1.5 l of dichloromethane, 13.3 g (0.13 mol) of neutral alumina and 28 g (0.13 mol) of pyridinium chlorochromate are added and the mixture is stirred at room temperature for 1 hour.

The suspension is filtered through 1 kg of silica gel 230-400 mesh in a glass suction filter, eluted without sucking dry using petroleum ether/ethyl acetate 3:1 and the eluate is concentrated to dryness in vacuo. Yield: 13.4 g (65% of theory) M.p.: 152° C.

Example VI 4-(4-Fluorophenyl)-6-isopropyl-5-methoxycarbonyl-1H-pyrrolo(2,3-b)pyridine

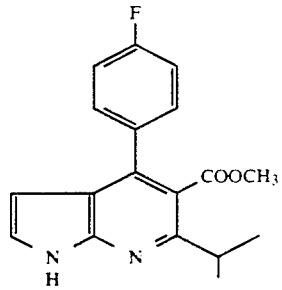

23.9 g (55 mmol) of a mixture of methoxymethyltriphenylphosphonium bromide and sodium amide are covered with a layer of 145 ml of anhydrous tetrahydrofuran and the mixture is stirred vigorously for 15 min. 17.4 g (55 mmol) of the compound from Example V are added to 145 ml of tetrahydrofuran and the mixture is stirred at room temperature for 1 h. A further 23.9 g (55 mmol) of methoxymethyltriphenylphosphonium bromide/sodium amide are added and the mixture is stirred at room temperature for 60 min. 185 ml (1.11 mol) of 6 M hydrochloric acid are added, and the mixture is heated to reflux for 1 h and cooled. It is neutralized using 5 M sodium hydroxide solution and the phases are separated. The aqueous phase is extracted twice with ethyl acetate, and the combined organic phases are washed with saturated sodium chloride solution, dried over sodium sulphate and concentrated to dryness. The residue which remains is dissolved in dichloromethane and added to a glass frit (porosity 3) which contains 450 g of silica gel 230–400 mesh. The mixture is eluted without sucking dry using a gradient of petroleum ether/ethyl acetate of 4:1 to 2:1. The eluate is concentrated to dryness in vacuo and the residue is thoroughly stirred in a mixture of ether/petroleum ether. Yield: 13.8 g (80% of theory) of colorless crystals M.p.: 187° C.

Example VII 4-(4-Fluorophenyl)-5-hydroxymethyl-6-isopropyl-1H-pyrrolo(2,3-b)pyridine

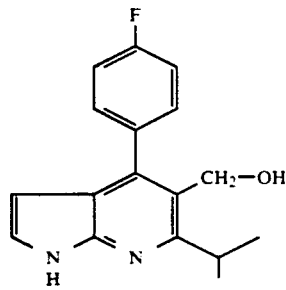

100 ml of a 1.5 M solution of diisobutylaluminum hydride in toluene are added slowly at −78° C. under argon to a suspension of 15.6 g (50 mmol) of the compound from Example VI in 700 ml of toluene, which leads to a clear solution. After 1 h, 40 ml of 1.5 M diisobutylaluminum hydride solution are added at the same temperature and the mixture is stirred for a further hour. It is warmed to 0°–5° C. using a water bath and stirred at this temperature for 1 h. 150 ml of water and 100 ml of ethyl acetate are cautiously added, and the mixture is stirred at room temperature for 1 h and filtered off with suction using kieselguhr. The phases are separated, the aqueous phase is extracted with ethyl acetate and the combined organic phases are washed with saturated sodium chloride solution. The solution is dried over sodium sulphate, concentrated to dryness in vacuo and the residue which remains is thoroughly stirred in dichloromethane.

Yield: 3.7 g

The kieselguhr residue is extracted by boiling twice with ethyl acetate and filtered off with suction. The filtrates are combined, washed with saturated sodium chloride solution, dried over sodium sulphate, concentrated in vacuo and the residue is stirred thoroughly in dichloromethane.

Yield 8.3 g,

Total yield: 12.0 g (84% of theory) of colourless crystals.

M.p.: 230° C.,

Example VIII 4-(4-Fluorophenyl)-5-formyl-6-isopropyl-1H-pyrrolo-[2,3-b]pyridine

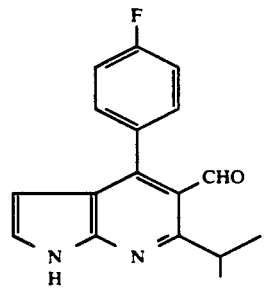

23.9 g (84 mmol) of the compound from Example VII are suspended in 1.6 l of dichloromethane, 17.1 g of neutral alumina and 36.1 g (168 mmol) of pyridinium chlorochromate are added and the mixture is stirred at room temperature for 1 h. The suspension is filtered through 1.2 kg of silica gel (230–400 mesh) in a glass suction filter and washed without sucking dry using petroleum ether/ethyl acetate 3:2. The eluate is concentrated to dryness in vacuo and the residue which remains is stirred thoroughly in ether.

Yield: 15.4 g (65% of theory) of colorless crystals, M.p. 190° C.

Example IX-a (E)-3-[4-(4-Fluorophenyl)-6-isopropyl-1H-pyrrolo[2,3-b]-pyridin-5-yl]prop-2-enal

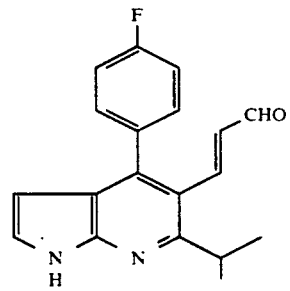

A solution of 11 g (42 mmol) of diethyl 2-(cyclohexylamino)-vinyl-phosphonate in 60 ml of tetrahydrofuran are added dropwise under argon in the course of 10 min to a suspension of 2.52 g (84 mmol) of 80% strength sodium hydride in 60 ml of anhydrous tetrahydrofuran. 9.9 g (35 mmol) of the compound from Example VIII dissolved in 100 ml of tetrahydrofuran are added dropwise at reflux. The mixture is allowed to boil under reflux for 90 min and is cooled, treated with water and extracted several times with ethyl acetate. The combined organic phases are washed with saturated sodium chloride solution and concentrated in vacuo. The residue is dissolved in 300 ml of toluene and heated under reflux for 1 h with 22.9 g (182 mmol) of oxalic acid dihydrate in 350 ml of water. The mixture is cooled, the phases are separated and the aqueous phase is extracted twice with ethyl acetate. The combined organic phases are washed with saturated sodium chloride solution, dried over sodium sulphate and concentrated to dryness in vacuo. The residue is dissolved in dichloromethane and filtered through 400 g of silica gel 230–400 mesh in a glass suction filter. The mixture is eluted without sucking dry using petroleum ether/ethyl acetate 1:1, the eluate is concentrated in vacuo and the residue is stirred thoroughly in ether.

Yield: 9.2 g (85% of theory) of colorless crystals, M.p.: 236° C.

Example IX-b (E)-3-[4-(4-Fluorophenyl)-6-isopropyl-1-methyl-1H-pyrrolo[2,3-b]pyridin-5-yl]prop-2-enal

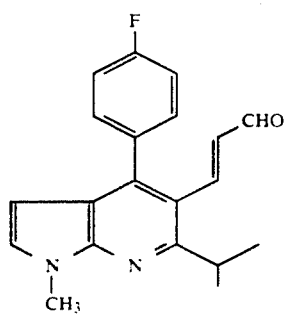

2 g (6.55 mmol) Of the compound from Example IX-a are dissolved in 40 ml of anhydrous dimethylformamide and 0.8 g (7.15 mmol) of potassium tert-butoxide is added. The mixture is stirred at room temperature for 15 min, 1.02 g (7.15 mmol) of methyl iodide are added and the mixture is stirred for a further 60 min at room temperature. It is poured into 150 ml of water, extracted several times with ethyl acetate, and the combined organic phases are washed with saturated sodium chloride solution, dried using sodium sulphate and concentrated to dryness in vacuo. The residue which remains is chromatographed in a column (⌀4 cm) on 100 g of silica gel 230-400 mesh using petroleum ether/ethyl acetate 5:1. The eluate is concentrated in vacuo and stirred thoroughly in ether/petroleum ether.

Yield: 1.15 g (54% of theory) of colorless crystals, M.p.: 125° C.

The compounds shown in Table 1 were prepared in analogy to Example IX-b:

TABLE 1

| Ex. No. | R | reagent | conditions | yield | M.p |
|---|---|---|---|---|---|
| IX-c | —CH(CH₃)₂ | I—CH(CH₃)₂ | 2 h 60° C. | 52% | 144° C. |
| IX-d | —CH₂—CN | Cl—CH₂—CN | 1 h RT, 1 h 60° C. | 19% | amorph. |
| IX-e | —CH₂—C≡CH | Br—CH₂—C≡CH 80% strength in toluene | 1 h RT | 60% | 87° C. |
| IX-f | —CH₂—CH₂—C₆H₅ | Br—CH₂—CH₂—C₆H₅ | 1 h RT +0.22 equiv. NaI 1 h RT, 1 h 60° C. | 31% | 146° C. |
| IX-g | —CH₂—C₆H₅ | Br—CH₂—C₆H₅ | 1 h RT | 85% | oil |
| IX-h | —CH₂—CH=CH₂ | Br—CH₂—CH=CH₂ | 1 h RT | 64% | 85° C. |
| IX-i | —CH₂—(3-pyridyl) | Cl—CH₂—(3-pyridyl) × HCl | x) | 28% | oil |
| IX-j | —CH₂—CH₂—CN | CH₂=CH—CN | xx) | 17% | 123° C. | x) Differing from the procedure of the example, the compound IX-i is prepared by stirring 2.5 equivalents of potassium tert-butoxide and 2.5 equivalents of the reagent shown at 60° C. for 2 h.
xx) Likewise differing from the procedure of Example IX-b, the compound IX-j is prepared by stirring 0.1 equivalent of potassium tert-butoxide and 2.4 equivalents of acrylonitrile at room temperature for 3 h.

PREPARATION EXAMPLES (GENERAL FORMULA I)

Example 1a

Methyl erythro-(E)-7-[4-(4-fluorophenyl)-6-isopropyl-1H-pyrrolo[2,3-b]pyridin-5-yl]3,5-dihydroxy-hept-6-enoate

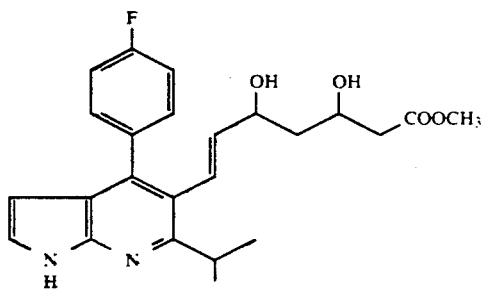

0.61 g (5.25 mmol) of methyl acetoacetate is added dropwise at 0-5° C. to a suspension of 0.32 g (10.5 mmol) of 80% strength sodium hydride in 10 ml of anhydrous tetrahydrofuran. After 15 min. 6.6 ml (10.85 mmol) of 15% strength butyllithium in hexane are added dropwise in the course of 10 min and the mixture is kept at 0°-5° C. for a further 15 min. 1.1 g (3.5 mmol) of the compound from Example IX-a in 10 ml of tetrahydrofuran are added to this mixture and it is stirred at room temperature for 45 min. It is then treated cautiously with 1.35 g (22.4 mmol) of acetic acid in 25 ml of water, extracted twice with ethyl acetate, and the combined organic phases are washed with saturated sodium chloride solution, dried over sodium sulphate and concentrated in vacuo. The residue which remains is dissolved in 20 ml of tetrahydrofuran. 4.2 ml (4.2 mmol) of a 1 M triethylborane solution in tetrahydrofuran is added and air is blown through the solution for 5 min. 0.16 g (4.2 mmol) of sodium borohydride are added at −78° C. 3.5 ml of methanol are then added dropwise and the mixture is kept at −78° C. to −75° C. for 1 h. It is then allowed to warm to room temperature, 11.6 ml of 30% strength hydrogen peroxide and 30 ml of water being added from −30° C. The mixture is extracted twice with ethyl acetate, and the combined organic phases are washed with saturated sodium chloride solution, dried over sodium sulphate and concentrated in vacuo. The residue which remains is chromatographed in a column (⌀3 cm) on 40 g of silica gel 230-400 mesh using petroleum ether/ethyl acetate 1:1. The eluate is concentrated in vacuo and stirred thoroughly in ether.

Yield: 0.65 (43% of theory),

M.p.: 163° C.

In analogy to Example I-a, the products shown in Table 2 are obtained from 7 mmol of sodium hydride, 5.25 mmol of ethyl acetate, 10.85 mmol of butyllithium and 3.5 mmol of the respective compound from Example IX-b-j, the mixture being worked up using 19 mmol of acetic acid.

TABLE 2

![structure]

| Ex. No. | R | Prepared from Example | Yield (%) | M.p. (°C.) |
|---|---|---|---|---|
| 1-b | —CH₃ | IX-b | 42 | 74 |
| 1-c | —CH(CH₃)₂ | IX-c | 38 | 101 |
| 1-d | —CH₂—CN | IX-d | 3 | amorph. |
| 1-e | —CH₂—C≡CH | IX-e | 13 | 88 |
| 1-f | —CH₂—CH₂—C₆H₅ | IX-f | 49 | 124 |
| 1-g | —CH₂—C₆H₅ | IX-g | 42 | 126 |
| 1-h | —CH₂—CH=CH₂ | IX-h | 37 | 104 |
| 1-i | —CH₂-pyridyl | IX-i | 25 | oil |
| 1-j | —CH₂—CH₂—CN | IX-j | 18% | oil |

Example 2-a

Sodium erythro-(E)-7-[4-(4-fluorophenyl)-6-isopropyl-1H-pyrrolo[2,3-b]pyridin-5-yl]-3,5-dihydroxy-hept-6-enoate

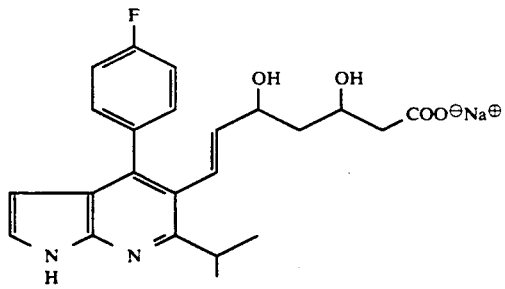

3.3 ml (0.33 mmol) of 0.1 M sodium hydroxide solution are added to a solution of 141 mg (0.33 mmol) of the compound from Example I-a in 3.3 ml of tetrahydrofuran and the mixture is stirred at room temperature for 1 h, concentrated to dryness in vacuo and dried over phosphorus pentoxide in a high vacuum.

Yield: 120 mg (83% of theory)

M.p.: 243° C. (dec.)

The compounds given in Table 3 were prepared in analogy to the procedure of Example 2-a:

TABLE 3

| Ex. No. | R | Yield (% of theory) | M.p. (°C.) | Starting compound |
|---|---|---|---|---|
| 2-b | —CH₃ | 94 | 231 (dec.) | 1-b |
| 2-c | 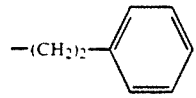 | 49 | 221 (dec.) | 1-c |
| 2-f | —(CH₂)₂—<phenyl> | 91 | 234 (dec.) | 1-f |
| 2-g | —CH₂—<phenyl> | 99 | 239 (dec.) | 1-g |
| 2-h | —CH₂—CH=CH₂ | 89 | 234 (dec.) | 1-h |

Example 3-b

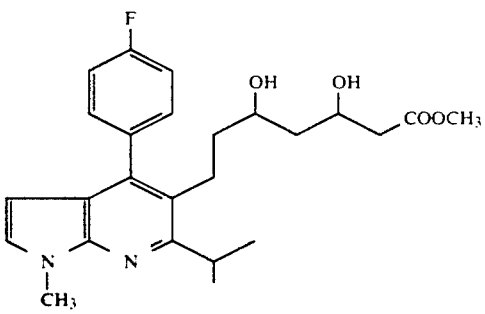

176 mg (0.4 mol) of the compound from Example 2 are dissolved in 30 ml of methanol and 20 μl of triethylamine and the solution is hydrogenated for 4.5 h at normal pressure and room temperature using 150 mg of 10% strength palladium/carbon. The catalyst is filtered off, the solution is concentrated to dryness and the residue is partitioned between ethyl acetate and saturated sodium chloride solution. The organic phase is dried, concentrated and crystallized from ether/petroleum ether.

Yield: 91 mg (51% of theory) of colorless crystals. M.p.: 97° C.

It will be understood that the specification and examples are illustrative but not limitative of the present invention and that other embodiments within the spirit and scope of the invention will suggest themselves to those skilled in the art.

We claim:

1. A substituted pyrrolo-pyridine of the formula

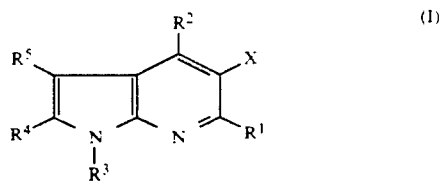

in which
R¹ represents straight-chain or branched alkyl having up to 8 carbon atoms, or represents cycloalkyl having 3 to 6 carbon atoms,
R² represents phenyl which is optionally monosubstituted or disubstituted by indentical or different substituents from the group consisting of straight-chain or branched alkyl having up to 6 carbon atoms, trifluoromethyl, hydroxymethyl, phenoxy, benzyl, benzyloxy and halogen,
R³ represents hydrogen, represents straight-chain or branched alkyl having up to 10 carbon atoms, which is optionally substituted by cyano, straight-chain or branched alkoxy having up to 6 carbon atoms, halogen, pyridyl, quinolinyl, furyl, thienyl, naphthyl or phenyl, each of which can in turn be substituted by halogen, cyano, nitro, or straight-chain or branched alkyl or alkoxy in each case having up to 6 carbon atoms, represents straight-chain or branched alkenyl or alkynyl in each case having up to 8 carbon atoms, or represents cycloalkyl having 3 to 6 carbon atoms or phenyl,
R⁴ and R⁵ are identical or different and represent hydrogen, or represent straight-chain or branched alkyl having up to 6 carbon atoms, which is optionally substituted by hydroxyl, halogen, cyano or alkoxy having up to 4 carbon atoms,
X represents a radical of the formula —A—B, in which
A denotes a group of the formula —CH₂—CH₂— or —CH=CH—,
B denotes a group of the formula

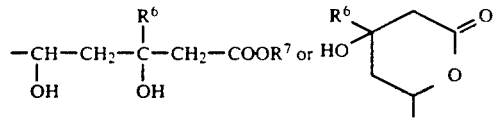

in which
R⁶ denotes hydrogen or straight-chain or branched alkyl having up to 10 carbon atoms
and
R⁷ denotes hydrogen or straight-chain or branched alkyl having up to 10 carbon atoms, which can be substituted by phenyl, or denotes aryl having 6 to 10 carbon atoms or a cation, or represents a radical of the formula

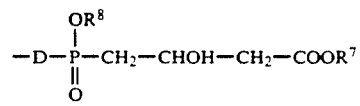

in which
D denotes a radical of the formula —(CH$_2$)$_t$, —CH=CH—, —C≡C— or —CH$_2$—O—, in which the latter is bonded to the phosphorus atom via O
R$^8$ denotes hydrogen or straight-chain or branched alkyl having up to 4 carbon atoms, and
t denotes the number 1 or 2,
or a salt thereof.

2. A substituted pyrrolo-pyridine according to claim 1,
in which
R$^1$ represents straight-chain or branched alkyl having up to 6 carbon atoms, or represents cyclopropyl, cyclopentyl or cyclohexyl,
R$^2$ represents phenyl which is optionally substituted by straight-chain or branched alkyl having up to 4 carbon atoms, trifluoromethyl, fluorine, chlorine or bromine,
R$^3$ represents straight-chain or branched alkyl having up to 8 carbon atoms, which is optionally substituted by cyano, straight-chain or branched alkoxy having up to 4 carbon atoms, fluorine, chlorine, bromine, pyridyl or phenyl, each of which can in turn be substituted by fluorine, chlorine, bromine cyano, nitro, straight-chain or branched alkyl or alkoxy in each case having up to 4 carbon atoms, represents straight-chain or branched alkenyl or alkynyl in each case having up to 6 carbon atoms, represents cyclopropyl, cyclopentyl, cyclohexyl or phenyl,
R$^4$ and R$^5$ represent hydrogen,
X represents a radical of the formula —A—B,
in which
A denotes a group of the formula —CH$_2$—CH$_2$— or —CH=CH—,
B denotes a group of the formula —CH—CH$_2$—C—CH$_2$—COOR$^7$ or HO
  |         |
  OH       OH
R$^6$ (with lactone form shown)

in which
R$^6$ denotes hydrogen
and
R$^7$ denotes hydrogen or straight-chain or branched alkyl having up to 8 carbon atoms or benzyl, or denotes phenyl or a cation,
or a salt thereof.

3. A substituted pyrrolo-pyridine according to claim 1,
in which
R$^1$ represents straight-chain or branched alkyl having up to 4 carbon atoms or cyclopropyl,
R$^2$ represents phenyl which is optionally substituted by methyl, trifluoromethyl, fluorine or chlorine,
R$^3$ represents hydrogen, represents straight-chain or branched alkyl having up to 6 carbon atoms, which is optionally substituted by cyano, methoxy, fluorine, pyridyl or phenyl, represents straight-chain or branched alkenyl or alkynyl in each case having up to 4 carbon atoms, or represents cyclopentyl or cyclohexyl,
R$^4$ and R$^5$ represent hydrogen,
X represents a radical of the formula —A—B, in which
A denotes a group of the formula —CH$_2$—CH$_2$— or —CH=CH—,
B denotes a group of the formula —CH—CH$_2$—C—CH$_2$—COOR$^7$ or HO
  |         |
  OH       OH
R$^6$ in which
R$^6$ denotes hydrogen
and
R$^7$ denotes hydrogen, methyl, ethyl, propyl, isopropyl, butyl, isobutyl, tert-butyl or benzyl, or denotes a sodium, potassium, calcium, magnesium or ammonium ion,
or a salt thereof.

4. A compound according to claim 1, wherein such compound is methyl 7-[1-allyl-4-(4-fluorophenyl)-6-isopropyl-1H-pyrrolo(2,3-b)pyridin-5-yl]3,5-dihydroxyhept-6-enoate of the formula 5. A compound according to claim 1, wherein such compound is methyl 7-[1-(2-cyanoethyl)-4-(4-fluorophenyl)-6-isopropyl-1H-pyrrolo(2,3-b)pyridin-5-yl]3,5 dihydroxyhept-6-enoate of the formula 6. A compound according to claim 1, wherein such compound is methyl 7-[1-cyanomethyl-4-(4-fluorophenyl)-6-isopropyl-1H-pyrrolo(2,3-b)pyridin-5-yl]3,5-dihydroxyhept-6-enoate of the formula

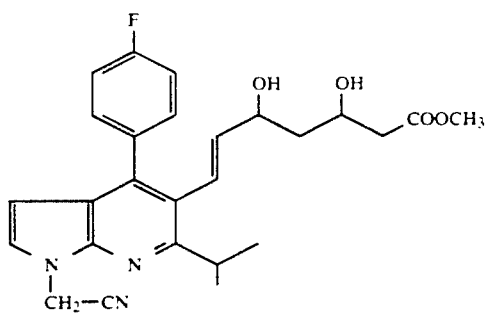

7. A compound according to claim 1, wherein such compound is 7-[4-(4-fluorophenyl)-1,6-diisopropyl pyrrolo(2,3-b)pyridin-5-yl]-3,5-dihydroxy-hept-6-enoic acid of the formula

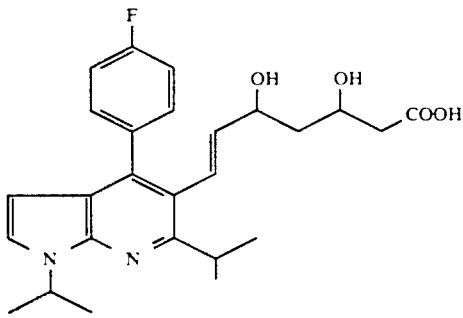

or a salt thereof.

8. A compound according to claim 1, wherein such compound is 7-[4-(4-fluorophenyl)-6-isopropyl-(1-phenethyl)pyrrolo(2,3-b)pyridin-5-yl]-3,5-dihydroxy-hept-6-enoic acid of the formula

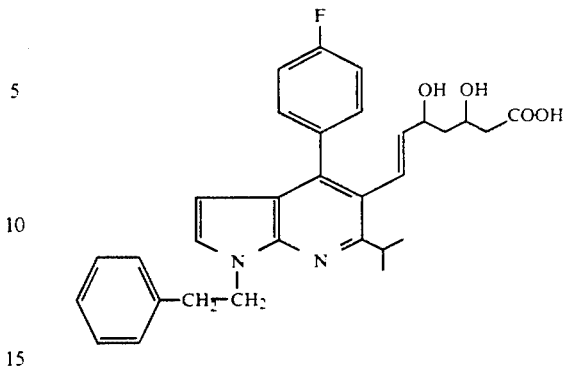

or a salt thereof.

9. A compound according to claim 1, wherein such compound is 7[1-allyl-4-(4-fluorophenyl)-6-isopropyl-pyrrolo(2,3-b)pyridin-5-yl]-3,5-dihydroxy-hept-6-en-1-oic acid of the formula

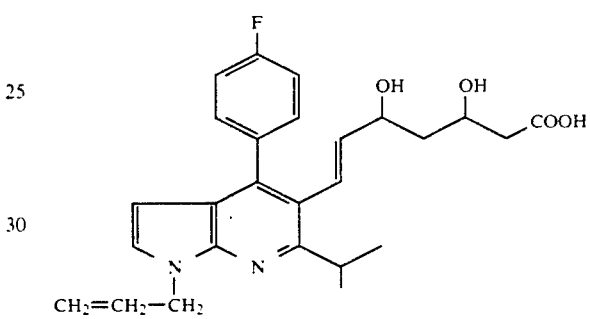

or a salt thereof.

10. A composition for treating hyperlipoproteinaemia, lipoproteinaemia or arteriosclerosis comprising an amount effective therefor of a compound or salt thereof according to claim 1 and a diluent.

11. A method of treating hyperlipoproteinaemia, lipoproteinaemia or arteriosclerosis which comprises administering to a patient suffering therefrom an amount effective therefor of a compound or salt thereof according to claim 1.

12. The method according to claim 11, wherein such compound is methyl 7-[1-allyl-4-(4-fluorophenyl)-6-isopropyl-1H-pyrrolo(2,3-b)pyridin-5-yl]3,5-dihydroxyhept-6-enoate, methyl 7-[1-cyanoethyl-4-(4-fluorophenyl)-6-isopropyl-1H-pyrrolo(2,3-b)pyridin-5-yl]3,5-dihydroxy-hept-6-enoate, methyl 7-[1-cyanomethyl-4-(4-fluorophenyl)-6-isopropyl-1H-pyrrolo(2,3-b)pyridin-5-yl]3,5-dihydroxy-hept-6-enoate, 1-isopropyl-7-[4-(4-fluorophenyl)-pyrrolo(2,3-b)pyridin-5-yl]-3,5-dihydroxy-hept-6-en-1-oic acid, 1-phenethyl-7-[4-(4-fluorophenyl)-pyrrolo(2,3-b)pyridin-5-yl]-3,5-dihydroxy-hept-6-en-1-oic or 1-allyl-7-[4-(4-fluorophenyl)-pyrrolo(2,3-b)pyridin-5-yl]-3,5-dihydroxy-hept-6-en-1-oic acid, or a salt thereof.

* * * * *

UNITED STATES PATENT AND TRADEMARK OFFICE
CERTIFICATE OF CORRECTION

PATENT NO. : 5,120,782

DATED : June 9, 1992

INVENTOR(S) : Hubsch et al.

It is certified that error appears in the above-identified patent and that said Letters Patent is hereby corrected as shown below:

Col. 33, line 20  Before " represents " insert -- represents hydrogen,--

Col. 34, line 26  Delete " I " and substitute -- 1 --

Col. 34, line 46  Delete " I " and substitute -- 1 --

Signed and Sealed this

Eighth Day of March, 1994

Attest:

BRUCE LEHMAN

*Attesting Officer*    *Commissioner of Patents and Trademarks*